(12) United States Patent
Cassiday et al.

(10) Patent No.: US 10,569,475 B2
(45) Date of Patent: Feb. 25, 2020

(54) IR TUBE SEALER AND METHODS SEALING A TUBE

(71) Applicant: SAINT-GOBAIN PERFORMANCE PLASTICS CORPORATION, Solon, OH (US)

(72) Inventors: Bryan Cassiday, Beaverton, MI (US); Anthony P. Pagliaro, Jr., Lansdale, PA (US); Jason B. Chapman, Clearwater, FL (US); Sridhar K. Siddhamalli, Lutz, FL (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 175 days.

(21) Appl. No.: 14/966,967

(22) Filed: Dec. 11, 2015

(65) Prior Publication Data

US 2016/0167289 A1 Jun. 16, 2016

Related U.S. Application Data

(60) Provisional application No. 62/091,159, filed on Dec. 12, 2014.

(51) Int. Cl.
*B29C 65/14* (2006.01)

(52) U.S. Cl.
CPC .................. *B29C 65/1412* (2013.01)

(58) Field of Classification Search
CPC ............ B29C 65/1412; B29C 65/1435; B29C 65/1445; B29C 65/1467; B29C 65/8253; B29C 66/1122; B29C 66/3472; B29C 66/43121; B29C 66/73921; B29C 66/81267; B29C 66/81427; B29C 66/8322; B29C 66/857; B29C 66/8614; A61M 39/14
USPC ....................................... 156/275.1
See application file for complete search history.

(56) References Cited

U.S. PATENT DOCUMENTS

| 3,989,778 | A | * | 11/1976 | Osborne | .............. | B23K 26/067 |
| | | | | | | 156/272.8 |
| 4,253,500 | A | | 3/1981 | Williams | | |
| 5,272,304 | A | | 12/1993 | Been et al. | | |
| 5,858,016 | A | | 1/1999 | Bacehowski et al. | | |

(Continued)

FOREIGN PATENT DOCUMENTS

| FR | 1560594 A | 3/1969 |
| JP | H01288422 A | 11/1989 |
| JP | 2004329223 A | 11/2004 |

OTHER PUBLICATIONS

International Search Report for PCT/US2015/065350 dated Apr. 5, 2016, 1 page.

(Continued)

*Primary Examiner* — Michael N Orlando
*Assistant Examiner* — Elizabeth Bradford
(74) *Attorney, Agent, or Firm* — Abel Schillinger, LLP; Chi Suk Kim

(57) ABSTRACT

Embodiments of the present disclosure are directed to an IR tube sealing device and method of sealing a polymer tube with infrared energy. In particular embodiments, the IR tube sealing device can be a portable, hand-held device adapted to receive and compress a polymer tube, and produce and direct infrared energy toward the compressed polymer tube to quickly form a permanent aseptic seal.

18 Claims, 8 Drawing Sheets

(56) References Cited

U.S. PATENT DOCUMENTS

| | | | | |
|---|---|---|---|---|
| 6,387,209 | B1* | 5/2002 | Nettesheim | B29C 65/1435 |
| | | | | 156/379.6 |
| 6,544,022 | B2 | 4/2003 | Lanser et al. | |
| 6,784,407 | B2 | 8/2004 | Wright et al. | |
| 7,006,763 | B2 | 2/2006 | Miller et al. | |
| 7,398,813 | B2 | 7/2008 | Ivansons et al. | |
| 7,462,256 | B2* | 12/2008 | Basque | B23K 26/032 |
| | | | | 156/379.6 |
| 7,553,391 | B2* | 6/2009 | Link | B29C 65/14 |
| | | | | 156/137 |
| 7,570,875 | B1* | 8/2009 | Groves | F26B 3/283 |
| | | | | 219/405 |
| 7,820,937 | B2* | 10/2010 | Perreault | B29C 65/1674 |
| | | | | 219/121.64 |
| 7,955,468 | B2 | 6/2011 | Beute et al. | |
| 2008/0023135 | A1* | 1/2008 | Ivansons | A61M 39/146 |
| | | | | 156/304.2 |
| 2008/0202669 | A1* | 8/2008 | Zemmouri | A61M 39/146 |
| | | | | 156/158 |
| 2008/0265561 | A1* | 10/2008 | Buchanan | A61M 39/18 |
| | | | | 285/21.1 |
| 2009/0139967 | A1* | 6/2009 | Baker | B23K 26/0096 |
| | | | | 219/121.63 |
| 2013/0312370 | A1 | 11/2013 | Mueller et al. | |

OTHER PUBLICATIONS

Supplementary Search Report for EP15867113, dated Jul. 24, 2018, 10 pages.

* cited by examiner

IR TUBE SEALER AND METHODS SEALING A TUBE

CROSS-REFERENCE TO RELATED APPLICATION(S)

This application claims priority under 35 U.S.C. § 119(e) to U.S. Patent Application No. 61/091,159 entitled "IR TUBE SEALER AND METHODS SEALING A TUBE," by Bryan L. Cassiday, et al., filed Dec. 12, 2014, which is assigned to the current assignee hereof and incorporated herein by reference in its entirety.

FIELD OF THE DISCLOSURE

The present disclosure relates to tube sealing apparatuses, and more particularly to, tube sealing apparatuses which seal through application of infrared energy.

RELATED ART

Tube sealing devices are known and have wide use within, for example, the biopharmaceutical industry. Current tube sealing devices use heat to melt a thermoplastic tube and form a seal. Such devices are generally known as thermal tube sealers.

These traditional thermal tube sealing devices have substantial drawbacks. Firstly, the use of thermal energy to melt the thermoplastic tube can cause inconsistent sealing and leakage. Further, the use of thermal energy to melt a thermoplastic tube can negatively interact with a sensitive fluid within the tube. Moreover the use of thermal energy to melt a thermoplastic tube is very energy intensive and as such limits the ability to for the tube sealing device to be portable. Still further, particular tubes, such as, for example, gamma irradiated or gamma sterilized TPV tubes are not able to be sealed by traditional thermal sealers. In addition, traditional thermal tube sealing devices exhibit prolonged sealing times.

The current inventors have developed a tube sealing device which overcomes these and other drawbacks of traditional tube sealing devices. For example, one embodiment of the present disclosure is directed to a tube sealing device which uses infrared energy to form a seal on a thermoplastic tube. Embodiments include such IR tube sealing devices that are portable and successively form leak proof seals in a thermoplastic tube faster than traditional heat tube sealing devices. Further embodiments are directed toward sealed IR tubes. The current inventors have surprisingly discovered that tubes sealed with infrared energy can form a greater variety and unique characteristics in the final sealed tube.

BRIEF DESCRIPTION OF THE DRAWINGS

Embodiments are illustrated by way of example and are not limited in the accompanying figures.

Figure 1:
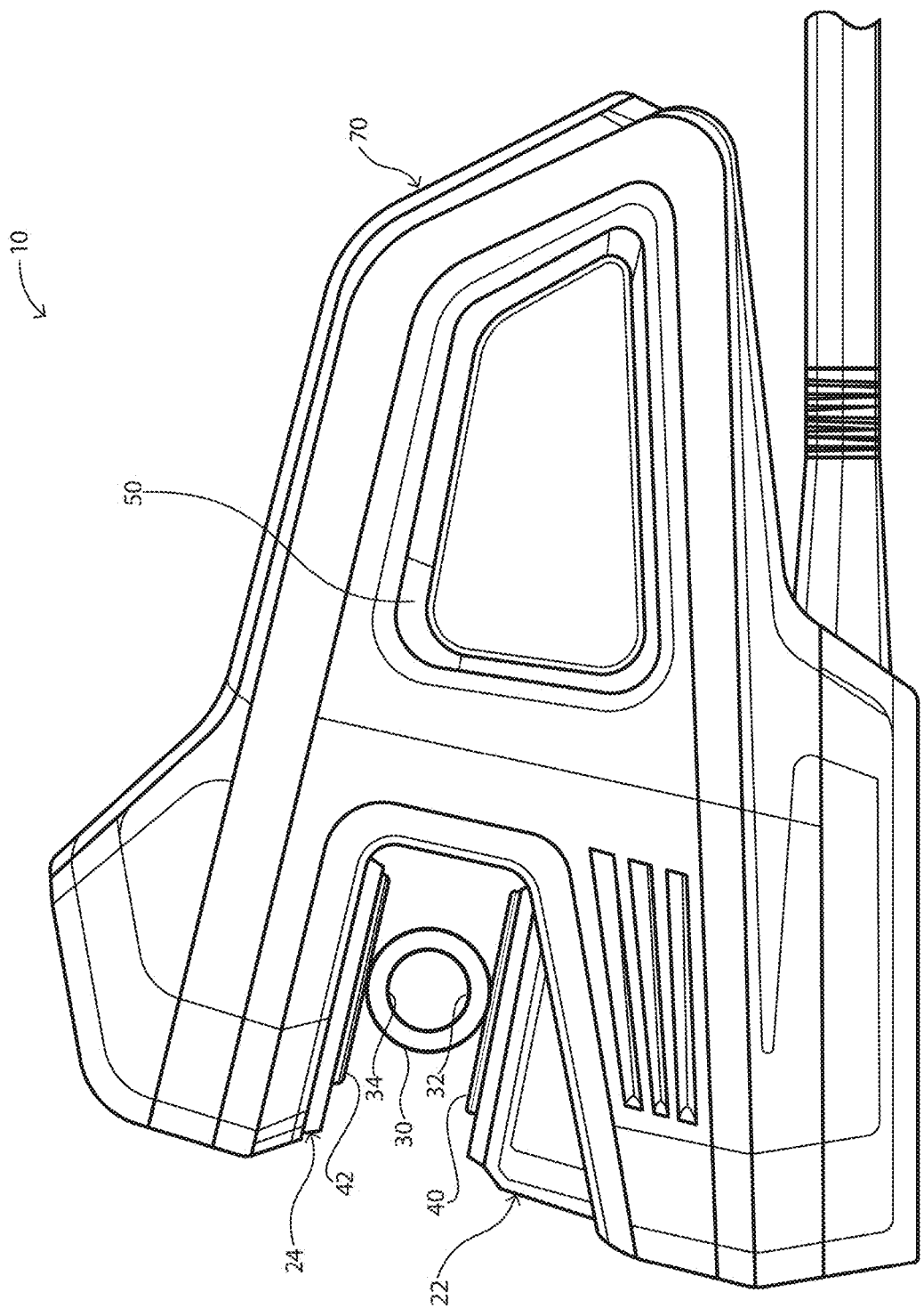
FIG. 1 includes an illustration of a perspective view of a portable IR tube sealing apparatus according to one embodiment.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the tube sealing arts.

Certain embodiments of the present disclosure are generally directed to infrared tube sealing devices and methods of sealing tubes using infrared energy. The IR tube sealing devices can have a faster seal time and greater seal efficiency than traditional thermal tube sealing devices, and in certain embodiments, can also be portable. The concepts are better understood in view of the embodiments described below that illustrate and do not limit the scope of the present invention.

Figure 2:
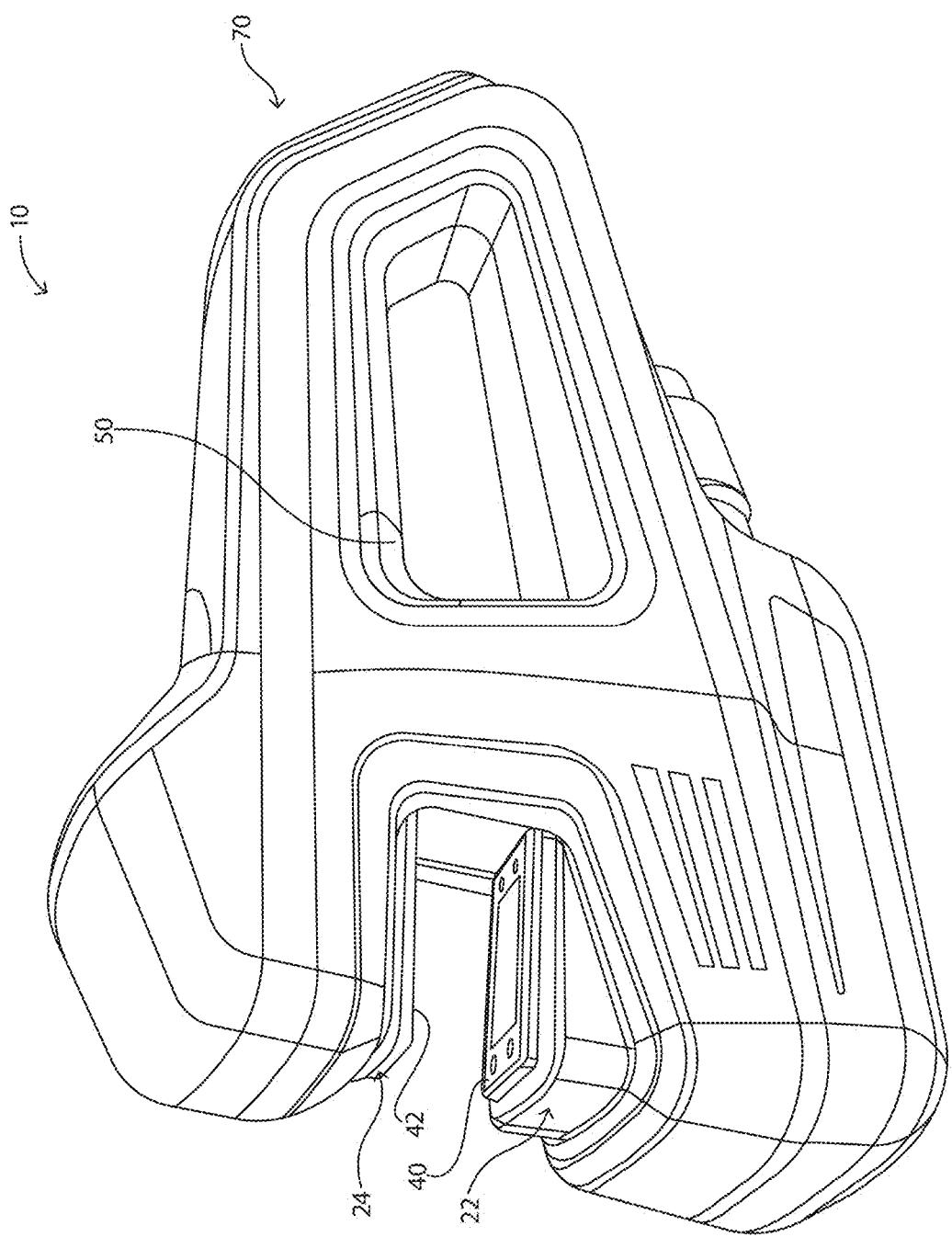
FIG. 2 includes an illustration of a side view of a portable IR tube sealing apparatus according to one embodiment.

Referring now to FIGS. 1-2, there is illustrated a handheld IR tube sealing apparatus 10 according to one embodiment. The IR tube sealing apparatus 10 can include a first IR lamp assembly 22 and a second IR lamp assembly 24 spaced apart from each other such that a tube 30 can be positioned between the first IR lamp assembly 22 and the second IR lamp assembly 24. This can be further seen in FIG. 3, which illustrates a front view of first and second IR lamp assemblies 22, 24 with a tube disposed therebetween. The IR lamp assemblies 22, 24 can be configured to produce and direct infrared energy towards the tube with enough energy to seal a thermoplastic tube. A particular advantage of certain embodiments of the present disclosure is the discovery that directing and concentrating infrared energy, as opposed to thermal or thermal energy can allow the tube sealer to quickly, more uniformly, and with less energy to permanently seal a thermoplastic tube.

The IR tube sealing apparatus can further include a first energy director and a second energy director. The first energy director can be adapted to direct and concentrate infrared energy emitted by the first IR lamp toward the space intended for the tube. Similarly, the second energy director can be adapted to direct and concentrate infrared energy emitted by the second IR lamp toward the space intended for the tube, and generally opposite from the first energy director. In certain embodiments, an IR lamp assembly can include an energy redirector configured to redirect energy from another IR lamp assembly back toward the space intended for the tube. For example, in particular embodiments, the first IR lamp assembly 22 can include an IR lamp and the second IR lamp assembly 24 can include an energy redirector, or vice versa, such that the apparatus includes a single IR lamp. An IR lamp assembly not including an IR lamp may also be referred to herein as an IR redirection assembly.

Figure 4:
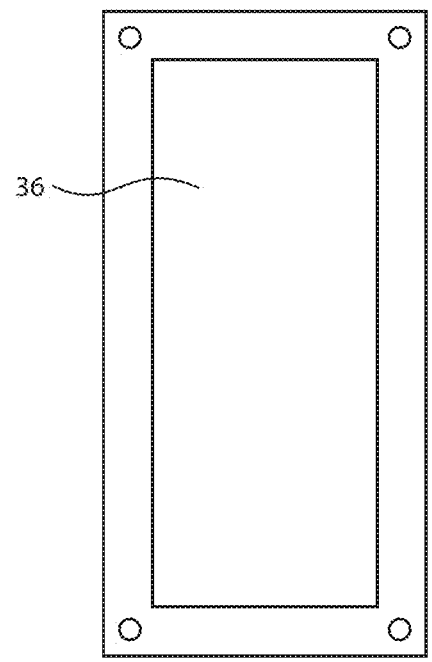
FIG. 4 illustrates a contact plate according to one embodiment.
Figure 5:
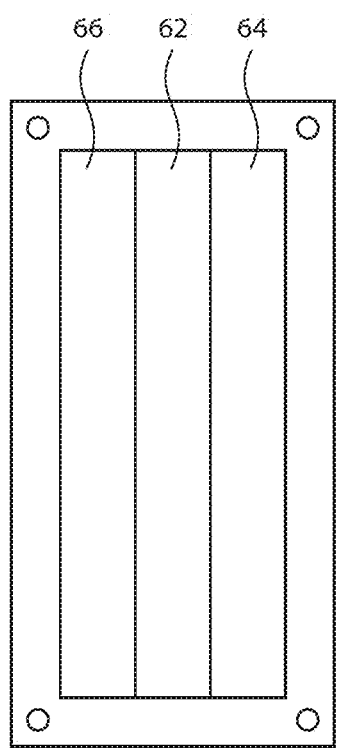
FIG. 5 illustrates a contact plate having a gradient according to one embodiment.

The IR tube sealing apparatus 10 can further include a first contact plate 40 and a second contact plate 42. For example, FIG. 4 illustrates a top view of a contact plate 40 or 42 according to one embodiment. The contact plates 40, 42 can be configured to contact the tube 30 and contain a seal region 36 which can allow the infrared energy produced by the IR lamp assemblies 22, 24 to substantially pass through the contact plates 40, 42 and interact with the tube 30. Further, in certain embodiments, the seal regions 36, 38 can be adapted to diffuse infrared energy within the seal region to achieve an even distribution of infrared energy throughout the seal region 36, 38. In other embodiments, as more particularly illustrated in FIG. 5, the seal region can be adapted to provide a greater amount of infrared energy in the central region 62, and a lower amount of infrared energy in the outer regions 64, 64 of the seal region. For example, the first and/or second contact plates 40, 42 can be adapted to provide a gradient amount of infrared energy across the seal region.

Figure 3:
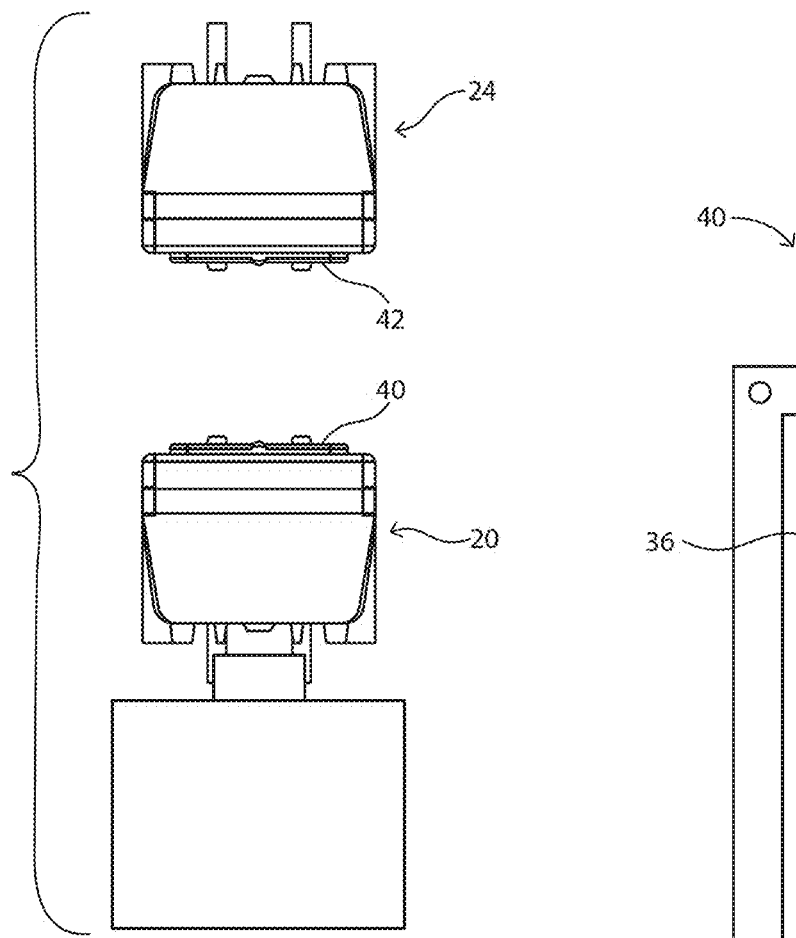
FIG. 3 includes an illustration of a front view of a first and second IR lamp assemblies with a tube disposed therebetween according to one embodiment.
Figure 7:
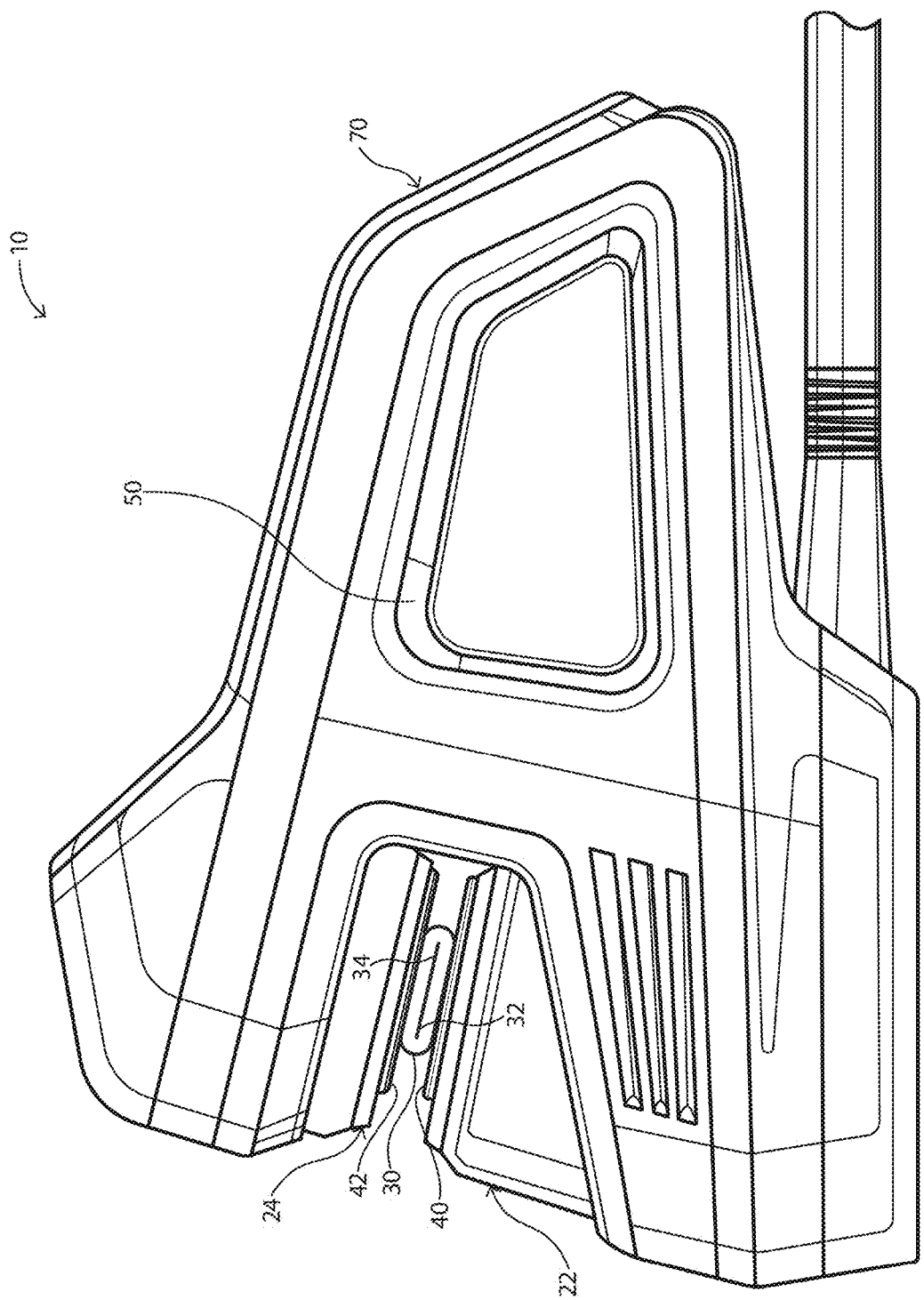
FIG. 7 includes an illustration of a side view of a portable IR tube sealing apparatus with a fully compressed polymer tube disposed therebetween according to one embodiment.

Referring again to FIGS. 1-2 and FIG. 7, the IR tube sealing apparatus 10 can be adapted to the squeeze or compress the tube 30 so that opposing inner sidewalls 32, 34 of the tube 30 move toward each other, and preferably contacting each other during sealing. For example, the first and/or second contact plate 40, 42 can be movable to thereby reduce the distance between the first contact plate 40 and the second contact plate 42. Referring to FIG. 3, which illustrates the IR tube sealing apparatus 10 compressing the tube 30, both the first and the second contact plates 40, 42 have shifted towards each other thereby compressing the tube 30 such that the inner opposing sidewalls 32, 34 contact each other.

Further, the first and/or second contact plates 40, 42 can be movable to accommodate various tube sizes as will be discussed in more detail below.

It is to be understood that in addition the to first and/or second contact plates 40, 42 either all of or even just a part of the first and/or second IR lamp assemblies can also be movable. Movement to allow the opposing sidewalls to touch can be initiated by a user pressing the button 50.

The apparatus described herein can be adapted to seal a wide variety of different tubes.

In particular embodiments, the apparatus described herein can be adapted to seal a biopharmaceutical tube. In fact, a particular advantage of certain embodiments of the present disclosure is the ability to quickly form high quality, robust seals suitable for sealing biopharmaceutical tubes where maintaining an aseptic seal is paramount. Accordingly, in certain embodiments, the apparatus can be adapted to seal a polymer tube which has an aseptic inner cavity. In further embodiments, the inner cavity of the polymer tube can remain aseptic during sealing. In such a way, the apparatus can be adapted to maintain the aseptic nature of the inner cavity of the polymer tube during sealing.

As non-limiting examples of suitable polymer tubes, and particularly biopharmaceutical tubes that the apparatus can be adapted to seal includes a thermoplastic tube, a thermoplastic elastomer (TPE) tube, a thermoplastic vulcanizate (TPV) tube, or combinations thereof. The tubes can be gamma irradiated, gamma sterilized, autoclaved, or unsterilized. In even more particular embodiments, the biopharmaceutical tubes can include gamma irradiated or gamma sterilized TPV tubes. In further embodiments, the polymer tube can include a reinforced thermoplastic elastomer such as a braided C-Flex® available from Saint-Gobain Performance Plastics Corporation (Clearwater, Fla., USA).

In particular embodiments, the IR tube sealing apparatus can be adapted to seal polymer tubes that could not be sealed with traditional thermal sealing devices. Examples of such polymer tubes that could not be sealed with traditional thermal sealing devices include TPV based tubes. Accordingly, in certain embodiments, the IR tube sealing apparatus can be adapted to seal a TPV based tube, such as a gamma irradiated or gamma sterilized TPV tube.

A particular advantage of certain embodiments of the present disclosure is the ability to form high quality, air tight, aseptic seals in tubing that is sensitive to degradation from high heat, high pressure, or both. For example, and as will be demonstrated by the examples below, tubes such as gamma irradiated or gamma sterilized TPV based tubes could not be sealed with traditional thermal sealers. The IR tube sealing apparatus can operate with In contrast, the present inventors surprisingly discovered that an IR tube sealing apparatus as described herein can form high quality, air tight, aseptic seals in such tubing material, while being able to maintain and even improve seal time. Further, the seal formed by an IR tube sealing apparatus as described herein can withstand high pressure as good as, or even better than, the tube wall itself. It was completely unexpected that such a high quality seal could be quickly formed by application of infrared energy to these types of polymer tubes as discussed herein.

In further embodiments, the apparatus can further be adapted to seal other tubes, such as tubes that could be sealed through traditional thermal sealers. For example, a particular advantage of certain embodiments of the present invention is to be able to seal a greater diversity of polymer tubes than was previously possible. Accordingly, in addition to the TPV tubes mentioned above, the apparatus described herein is further adapted to seal other types of polymer tubes, such as most thermoplastic tubes such as thermoplastic elastomer tubes. Further, as will be discussed in more detail below, the apparatus described herein is able to seal such thermoplastic tubes much more quickly than was previously possible.

Another way to describe the types of polymer tubes that the apparatus can be adapted to seal is its durometer hardness. Durometer Hardness of a polymer tube can be measured according to ASTM D2240. Durometer, like many other hardness tests, measures the depth of an indentation in the material created by a given force on a standardized presser foot. This depth is dependent on the hardness of the material, its viscoelastic properties, the shape of the presser foot, and the duration of the test. ASTM D2240 durometers allows for a measurement of the initial hardness, or the indentation hardness after a given period of time. The basic test requires applying the force in a consistent manner, without shock, and measuring the hardness (depth of the indentation). If a timed hardness is desired, force is applied for the required time and then read.

Accordingly, the apparatus can be adapted to seal a polymer tube having a Shore A hardness of at least 30 durometer, at least 35 durometer, or even at least 40 durometer as measured according to ASTM D2240. In further embodiments, the apparatus can be adapted to seal a polymer tube having a Shore A hardness of no greater than 100 durometer, no greater than 90 durometer, or even no greater than 80 durometer as measured according to ASTM D2240. Moreover, in still further embodiments, the apparatus can be adapted to seal a polymer tube having a Shore A hardness in a range of any of the minimum and maximums provided above, such as in a range of 30 durometer to 100 durometer, 35 durometer to 90 durometer, or even 40 durometer to 80 durometer as measured according to ASTM D2240.

In certain embodiments, the IR tube sealing apparatus can be adapted to produce desirable seal dimensions. For example, the seal dimensions can be a function of the radiation strength, the profile of the contact plate, the concentration and profile of radiation energy being reflected and/or the mechanism adapted to reduce the internal diameter of the tube. As used herein, the seal dimensions described and reported herein are measured as a full seal dimensions.

Figure 6:
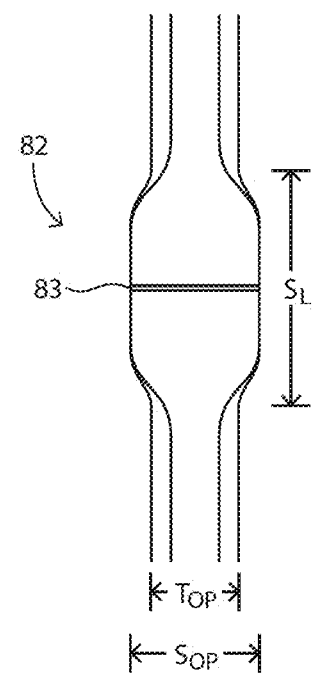
FIG. 6 illustrates a sealed tube according to one embodiment.

Accordingly, in certain embodiments, the apparatus can be adapted to form a seal having a desired seal dimension. Referring to FIG. 6, which illustrates a top view of a sealed tube, the seal can have a ratio of the seal length $S_L$ to outside diameter of the unsealed tube $T_{OD}$ of at least about 0.5, at least about 0.9, at least about 1.1, at least about 1.5, or even at least about 2.0. In further embodiments, the seal can have a ratio of the seal length $S_L$ to outside diameter of the unsealed tube $T_{OD}$ of no greater than 10, no greater than 8, or even no greater than 5. Moreover, the seal can have a ratio of the seal length $S_L$ to outside diameter of the unsealed tube $T_{OD}$ in a range of any of the minimum and maximum values provided above, such as in a range of from 0.5 to 10.

In certain embodiments, the IR tube sealing apparatus can be adapted to form a seal having a particular ratio of the seal outside diameter $S_{OD}$ to the outside diameter of the unsealed tube $T_{OD}$. For example, in certain embodiments, the seal can having a ratio of seal outside diameter $S_{OD}$ to the outside diameter of the unsealed tube $T_{OD}$ of at least about 1.01, at least about 1.1, at least about 1.2, or even at least about 1.3. In further embodiments, the seal can have a ratio of seal outside diameter $S_{OD}$ to the outside diameter of the unsealed tube $T_{OD}$ of no greater than 5, no greater than 3, or even no greater than 2. Moreover, the seal can have a ratio of seal outside diameter SOD to the outside diameter of the unsealed tube $T_{OD}$ in a range of any of the minimums and maximums provided above, such as in a range of from 1.01 to 5.

In certain embodiments, the seal can have a desirable length. For example, traditional thermal sealers suffered in the ability to create seals having a length of greater than 0.5 inches. Any larger than 0.5 inches would take a tremendous amount of time to form the long seal without completely melting the middle and damaging the seal quality. In contrast, the current inventors have surprisingly discovered that the temperature profile experienced by a tube during sealing through infrared energy can create tubes having uniquely longer seals. Accordingly, in particular embodiments, the seal can have a seal length of at least about 0.25 inches, at least about 0.51 inches, at least about 0.6 inches, at least about 0.7 inches, at least about 0.8 inches, at least about 0.9 inches, or even at least about 1 inch. In further embodiments, the seal can have a seal length of no greater than about 6 inches, no greater than about 4 inches, or even no greater than about 3 inches.

A particular advantage of certain embodiments of the present disclosure is the ability to quickly form a strong seal having the seal dimensions described herein. To create seals of the quality and dimensional characteristics described herein, traditional devices required either a much longer sealing time, otherwise the heat build up from traditional devices to obtain such a seal size in a reduced time could destroy the seal.

Referring again to FIG. 6, in certain embodiments, the seal region 82 can include an approximate mid-line indicator 83 to help a user identify the proper location to cut the seal in half while maintaining high quality seals on both sides of the severed tube. In particular embodiments, the mid-line indicator 83 can be a depressed groove, a raised channel, an indicia of a different color, or any other indicator that can be readily identifiable by a user. In particular embodiments, the apparatus can be adapted to form the mid-line indicator during or after the formation of the seal.

A particular advantage of certain embodiments of the present disclosure is the ability to quickly form a high quality permanent seal for a polymer tube. The quality of the seal can be described according to a number of different tests that illustrate the permanence and reliability of the seal. For example, the quality of the seal can be tested for aseptic characteristics, air tightness, visually inspected for defects such as defects or tears or cracks or holes, Total Organic Carbon content, Non-Volatile Reside content, extractable content, particulate analysis, pH, conductivity or combinations thereof.

Accordingly, in certain embodiments, the apparatus can be adapted to form an essentially aseptic seal. As used herein, the phrase "aseptic seal" refers to a seal capable of essentially preventing microbial ingress into the inside diameter of a polymer tube through the seal.

In further embodiments, the apparatus can be adapted to form an essentially airtight seal. As used herein, to determine whether a seal is essentially airtight, the seal can be tested with an air pressure of 15 psi for 30 minutes. The full seal is cut in half and both sides of the seal are pressured tested as indicated above. If the seal has no air leaks on both sides, the seal is considered essentially airtight for the tested rating.

Accordingly, in certain embodiments, the polymer tube can have an airtight seal having an airtight seal strength of at least 3 psi, at least 5 psi, at least 10 psi, at least 15 psi for 30 minutes. In other embodiment, the apparatus can be adapted to form a seal having an airtight rating of at least about 20 psi for 30 minutes, at least ab out 25 psi for 30 minutes, at least about 30 psi for 30 minutes, at least about 40 psi for 30 minutes, at least about 50 psi for 30 minutes, or even at least about 60 psi for 30 minutes. In still further embodiments, the apparatus can be adapted to form a seal having an airtight rating of at least about 15 psi for 60 minutes, at least about 20 psi for 60 minutes, at least ab out 25 psi for 60 minutes, at least about 30 psi for 60 minutes, at least about 40 psi for 60 minutes, at least about 50 psi for 60 minutes, or even at least about 60 psi for 60 minutes.

In further embodiments, the seal quality can be analyzed through visual inspection under magnification and have a low level of defects. As used herein, defects are referred to air bubbles, tears, cracks, or holes having a longest dimension of at least 0.5 mm. Accordingly, in certain embodiments, the apparatus can be adapted to produce a seal which is essentially free of defects having a longest dimension of at least 0.5 mm. For example, the seal can have a content of defects having a longest dimension of at least 0.5 mm of no greater than 10 defects per square centimeter, no greater than 5 defects per square centimeter, no greater than 3 defects per square centimeter, no greater than 2 defects per square centimeter, or even no greater than 1 defects per square centimeter. To determine the existence or content of defects, the seal region should be analyzed and measured at three different locations within the seal region, and the number of defects measured in each location added and averaged.

Other characteristics that can be used to describe the seal quality of seals made according to the present disclosure can meet various United States Pharmacopoeia standards including:

a. sub visible particles as measured according to United States Pharmacopoeia standard <788>;
b. pH as measured according to United States Pharmacopoeia standard <661>;
c. conductivity as measured according to United States Pharmacopoeia standard <645>;
d. NVR as measured according to United States Pharmacopoeia standard <661>;
e. Endotoxin as measured according to United States Pharmacopoeia standard <85>;
f. Cyotoxicity as measured according to United States Pharmacopoeia standard MEM elution;
g. Ames genotoxicity as measured according to ISO 10993-3;
h. Total organic carbon (TOC) as measured according to United States Pharmacopoeia standard <643; or
i. combinations thereof.

Yet another benefit of certain embodiments of the present disclosure is the ability form high quality seals that do not greatly suffer from performance characteristics after aging.

For example, in certain embodiments, the apparatus can be adapted to form a sealed tube that maintains a satisfactory air pressure test rating after aging. In particular embodiments, the sealed tube can have an air pressure test rating of at least about 3 psi, at least about 5 psi, at least about 8 psi, at least about 10 psi, at least about 12 psi, or even at least about 15 psi at 30 minutes. The aged air test rating can be completed under 1 of the following 3 test conditions:

Aged Pressure Test Condition 1—A fresh tube is sealed and then aged. The tube is cut in half and the half seal integrities of both portions are measured for the pressure test rating.

Aged Pressure Test Condition 2—A fresh tube is sealed, cut in half, and then both halves are aged. The half seal integrities of both portions are measured for the pressure test rating after aging.

Aged Pressure Test Condition 3—An aged tube is seal and the cut in half. The half seal integrities of both portions are measured for the pressure test rating after aging. Passing occurs for a particular pressure rating when both halves pass.

Accordingly, in particular embodiments, the sealed tube can have an aged pressure test rating of at least about 3 psi, at least about 5 psi, at least about 8 psi, at least about 10 psi, at least about 12 psi, or even at least about 15 psi at 30 minutes as measured under Aged Pressure Test Condition 1, Aged Pressured Test Condition 2, Aged Pressure Test Condition 3, or combinations thereof. Further, the sealed tube can have the recited pressure ratings under the recited aged pressure test conditions after natural aging at ambient conditions for 6 months, 1 year, 18 months, 2 years, or even 3 years. Further, in certain embodiments, the sealed tube can have the recited pressure ratings under the recited aged pressure test conditions after simulated aging at 55 degrees Celsius for 20 days, 40 days, 60 days, 80 days, or even 120 days according to ASTM F1980. It is to be understood that the simulated aging equates 1 year of natural aging to 40 days of simulated aging.

In even further embodiments, the sealed tube can have any combination of the above recited sealed tube characteristics recited above, such as passing tests including sub visible particulates, pH, conductivity, NVR, endotoxin, cytotoxicity, Ames genotoxicity, or TOC after aging under any of the test conditions recited above, and for any of the aging timeframes recited above, including simulated and natural aging.

As discussed above, in certain embodiments, the tube sealing apparatus can be adapted to apply, at least, infrared radiation to effect sealing of the polymer tube. Infrared radiation can be produced from, for example, an incandescent bulb within the IR lamp assembly. In particular embodiments, the incandescent bulb can be located at the focal point of a reflector, and preferably a parabolic reflector, to produce a collimated output which is directed toward the seal area to soften and fuse the polymer material throughout the seal region. In particular embodiments, the apparatus can be adapted to output infrared radiation toward the seal region from at least two different output sources. For example, and referring to FIGS. 1-2, certain embodiments of the apparatus can contain two incandescent bulbs and two independent set of reflectors disposed generally opposite each other within the first and second IR lamp assemblies respectively. By directing infrared radiation to two discrete, and preferably opposing, regions of the polymer tube, the seal time can be reduced while maintaining or even improving the seal quality.

Another unique characteristic of the apparatus and methods described herein is the discovery that the application of sealing energy, such as infrared energy, can begin before the tubing is fully compressed. For example, traditional thermal sealers could not initiate the application of thermal energy until the tube was fully compressed, due in part to the temperature profile and inherent results of application of thermal energy to seal tubes. Initiating application of thermal energy before fully compressing the tube could lead to seal failure. In contrast, the present inventors have surprisingly discovered that the application of infrared energy can begin before fully compressing the tube, and thus shorten cycle time. Without wishing to be bound by theory, it is believed that the unique temperature profile and sealing methodology created by application of infrared energy allows for the ability to initiate application of sealing energy before fully compressing the tube without risking seal failure. For example, it is believed that the temperature profile across the tube during sealing is more gradual than accomplished with a thermal sealer, preventing the outer surface of the tube from immediately nearing a melting point during application of energy. Since the outer surface is more stable during the initial application of infrared energy, the tube does not have to be fully compressed before initiating the application of infrared energy.

Accordingly, in certain embodiments, the apparatus can be adapted to initiate application of infrared energy before fully compressing the tube. Further, methods according to certain embodiments can include initiating application of infrared energy before fully compressing the tube.

In certain embodiments, and as particularly illustrated in FIG. 1, the IR tube sealing apparatus can adapted to be portable. As used herein, the phrase "portable" refers to an apparatus that has a weight of less than about 10 lbs, and is adapted to be transported and operated by a single hand of a user. In such embodiments, and referring in particular to FIG. 1, the IR tube sealing apparatus can further comprises a handle 70. The handle 70 can be adapted to receive at least one hand of a user, and support the user in transporting the IR tube sealing apparatus. Moreover, in particular embodiments, the button 50 can be positioned on the handle 70, such that a user can hold the IR tube sealing apparatus and press the button, such as with their index finger, at the same time.

In certain embodiments, the IR tube sealing apparatus can be adapted to operate using an internal power source, such as a battery, or can contain a power cord to plug into an electrical grid. In particular embodiments, the apparatus can be adapted to operate using an internal power source, such as a battery. A particular advantage of certain embodiments of the present disclosure is the creation of an IR tube sealing apparatus that can operate to seal a multitude of tubes without being connected to an external power source. In particular, it was discovered that devices employing infrared radiation as described herein can require a significantly lower amount of power to perform a sealing cycle, which has partly allowed for an effective portable tube sealing apparatus.

As discussed throughout this document, embodiments of the apparatus can include an apparatus that is adapted to quickly permanently seal a polymer tube. To quantify the sealing time, a Sealing Time Test can be employed. The sealing time test is performed by measuring the amount of time between initiation and removal of the seal from the device. The sealing time includes the time it takes to compress the tube, irradiate the tube, cool the tube, and release the tube. The variables of the Sealing Time Test are thus the type of polymer tube being sealed, and its dimensions, i.e. inner and outer diameter. For example, it generally requires more time to seal larger and thicker tubes. Thus, to normalize the test and compare different tube sealing apparatuses, the tube sealing characteristics, a specific inside diameter, outside diameter, and polymer type are standardized under various testing conditions outlined below.

Sealing Time Test Condition 1—Under this test condition a C-flex polymer tube under the trade name C-Flex® obtainable from Saint-Gobain Performance Plastics Corporation is employed. The tube has an inside diameter in a range of about 0.125 inches to 1 inch, and an outside diameter in a range of about 0.25 inches to 1.5 inches.

Sealing Time Test Condition 2—Under this test condition a C-flex polymer tube under the trade name C-Flex® obtainable from Saint-Gobain Performance Plastics Corporation is employed. The tube has an inside diameter of about 0.125 inches, and an outside diameter of about 0.25 inches.

Sealing Time Test Condition 3—Under this test condition a C-flex polymer tube under the trade name C-Flex® obtainable from Saint-Gobain Performance Plastics Corporation is employed. The tube has an inside diameter of about 0.25 inches, and an outside diameter of about 0.375 inches.

Sealing Time Test Condition 4—Under this test condition a C-flex polymer tube under the trade name C-Flex® obtainable from Saint-Gobain Performance Plastics Corporation is employed. The tube has an inside diameter of about 0.375 inches, and an outside diameter of about 0.5 inches.

Sealing Time Test Condition 5—Under this test condition a C-flex polymer tube under the trade name C-Flex® obtainable from Saint-Gobain Performance Plastics Corporation is employed. The tube has an inside diameter of about 0.5 inches, and an outside diameter of about 0.75 inches.

Sealing Time Test Condition 6—Under this test condition a C-flex polymer tube under the trade name C-Flex® obtainable from Saint-Gobain Performance Plastics Corporation is employed. The tube has an inside diameter of about 1 inch, and an outside diameter of about 1.5 inches inches.

Accordingly, in certain embodiments, the apparatus can be adapted to have a seal time of no more than 150 seconds, no more than 140 seconds, no more than 130 seconds, no more than 120 seconds, no more than 110 seconds, no more than 100 seconds, no more than 90 seconds, no more than 80 seconds, no more than 70 seconds, 60 seconds, no more than 55 seconds, no more than 50 seconds, no more than 45 seconds, no more than 40 seconds, no more than 35 seconds, no more than 30 seconds, or even no more than 25 seconds as measured according to the Sealing Time test under Sealing Time Test Condition 1, Sealing Time Test Condition 2, Sealing Time Test Condition 3, Sealing Time Test Condition 4, Sealing Time Test Condition 5, Sealing Time Test Condition 6, or combinations thereof.

A particular advantage of certain embodiments of the present disclosure is the ability for a tube sealing apparatus to exhibit such a short seal time as described above. For example, traditional thermal sealers required a substantial cool down period which limited the ability to form an aseptic quality permanent seal in under the time frames provided above, particular with a tube having the dimensions as described above in any of the sealing time test conditions 1-4.

Another way to describe certain improvements in embodiments of the present disclosure is the ability of the apparatus to perform a large number of consecutive sealing cycles while disconnected from an external power source. To quantify the number of consecutive sealing cycles that can be performed while disconnected from an external power source, the Consecutive Sealing Cycle Time Test can be utilized. Under this test, the number of consecutive sealing cycles that the apparatus can perform is determined by charging the tube sealer to full power, disconnecting from an external power source, and performing consecutive a seal cycle as discussed above until an aseptic quality seal can no longer be produced. The external variables included in this test are the type of polymer tube, and the tube's inner and outer diameter. For example, it requires more energy and more power to seal larger and thicker tubes. Thus, to test and compare the tube sealing characteristics, a specific inside diameter, outside diameter, and polymer type are normalized under various testing conditions outlined below.

Consecutive Battery Sealing Test Condition 1—Under test condition 1, a C-flex polymer tube obtainable from Saint-Gobain Performance Plastics Corporation is employed. The tube has an inside diameter of about 0.25 inches, and an outside diameter of about 0.375 inches.

Consecutive Battery Sealing Test Condition 2—Under test condition 2, a C-flex polymer tube obtainable from Saint-Gobain Performance Plastics Corporation is employed. The tube has an inside diameter within a range of from 0.125 inches to about 0.25 inches, and an outside diameter in a range of from about 0.250 inches to about 0.375 inches.

Consecutive Battery Sealing Test Condition 3—Under test condition 3, a C-flex polymer tube obtainable from Saint-Gobain Performance Plastics Corporation is employed. The tube has an inside diameter within a range of from 0.25 inches to about 0.5 inches, and an outside diameter in a range of from about 0.375 inches to about 0.750 inches.

Accordingly, in certain embodiments, the apparatus can be adapted to perform at least 25, at least 30, at least 35, at least 40, at least 45, at least 50, at least 55, at least 60, at least 65, at least 70, or even at least 75 consecutive sealing cycles while not being physically connected to an external power source as measured by the consecutive sealing cycle time test under Consecutive Battery Sealing test condition 1, Consecutive Battery Sealing test condition 2, Consecutive Battery Sealing test condition 3, or combinations thereof.

A particular advantage of certain embodiments of the present disclosure is the ability to form consecutive aseptic permanent seals without being connected to an external power source. For example, traditional thermal sealers were energy intensive thus limiting their ability to form the high number of seals provided above while disconnected from an external power source, while also being portable. In contrast, the current inventors have developed an IR tube sealing apparatus capable which is less energy intensive allowing for multiple aseptic permanent seals to be formed with disconnected from an external power source.

In certain embodiments, the apparatus can be adapted to quickly cool after formation of a permanent seal. In fact, a particular advantage of certain embodiments of the present disclosure is the shortened time between competition of a formed seal and the release of the mechanism adapted to reduce the distance between opposing side walls of the polymer tube, such as movable lamp assemblies and/or contact plates. In traditional devices designed to permanently seal a polymer tube through thermal energy, a much higher sealing temperature was required to obtain a robust seal, necessitating a long cool down period where the mechanism adapted to reduce the distance between opposing side walls must remain engaged, and the polymer tube can not be handled or else the seal would be damaged or even completely destroyed. In contrast, embodiments of the IR tube sealing apparatus described herein do not require such a long cool down period, leading to a significantly improved total seal time.

Accordingly, in certain embodiments, the apparatus can be adapted to release the force applied by the mechanism within a shorter amount of time necessary in a thermal tube sealer. For example, in particular embodiments, the IR tube sealing apparatus can be adapted to release the polymer tube within 60 seconds, within 50 seconds, within 45 seconds, within 40 seconds, within 35 seconds, within 30 seconds, within 25 seconds, within 20 seconds, within 15 seconds, within 10 seconds, or even within 5 seconds after stopping irradiating the seal region of the tube with infrared energy and the seal region can remain intact with a quality seal.

Moreover, in certain embodiments, the apparatus can be adapted to initiate cooling earlier than traditional thermal tube sealers. For example, traditional thermal tube sealers could not begin cooling with air pressure immediately after application of thermal energy due to the temperature profile created by the thermal sealing. In contrast, the present inventors have surprisingly discovered that the air pressure cooling can be initiated immediately after, and even during the application of infrared energy. Without wishing to be bound be theory, it is believed the unique temperature profile created allows for the application of air pressurized cooling earlier without risk of damaging the seal. Accordingly, total cycle time can be reduced.

As such, in certain embodiments, the apparatus and methods described herein can be adapted to initiate air pressure cooling immediately after application of thermal energy. In further embodiments, the apparatus can be adapted to initiate air pressure cooling while still applying infrared energy.

In certain embodiments, the apparatus can be adapted to wet seal or dry seal a polymer tube. As used herein, the phrase "wet seal" or "wet sealing" refers to sealing a polymer tube while fluid is present within the tube, whereas "dry seal" or "dry sealing" refers to sealing a polymer tube without the fluid present in the tube. Traditional thermal sealers can not adequately seal polymer tubes while wet without the risk of contamination and poor seal quality. Accordingly, a particular advantage of certain embodiments of the present disclosure is the ability for the apparatus described herein to form a high quality aseptic seal when the tube is wet and thus the apparatus is adapted to wet seal a polymer tube.

Further, the IR tube seal length of embodiments of the IR tube seal described herein is at least about twice the heat seal length, as shown in the following examples, and the IR tube seal can form a molecular bond at the tubing interface. Thus, an IR tube seal described herein can have the advantage of being more stable over time. For example, an IR tube seal described herein can exhibit an extended shelf life as compared to heat seals. Also, IR tube seals formed on aged seals can be stronger and more stable than heat seals.

Furthermore, it is a particular advantage of certain embodiments described herein that the IR sealing process does not have a negative impact on the original extractable characteristics of the tubing being sealed. For example, in certain embodiments, the IR tube sealing as described herein does not add to or deleteriously alter the base or original extractable/leachable profile of the tubing being sealed. In particular embodiments, an IR sealed tube described herein can satisfy at least one of the following standards for extractable/leachable testing: BPSA, BPOG, USP 661, EP 3.1.9, ASME-BPE, ASTM E55, or any combination thereof.

Another aspect of certain embodiments of the present disclosure is directed to a method of sealing a polymer tube. In general, the method can include providing an IR tube sealing apparatus as described in one more of the embodiments above; inserting a polymer tube into the apparatus; reducing the distance between opposing side walls of the polymer tube to define a seal region, irradiating the polymer tube with, at least, infrared energy to thereby form a seal; and releasing the polymer tube.

It is to be understood that the embodiments of the apparatus and its capabilities described above equally apply to the embodiments directed to methods of sealing a polymer tube. Accordingly, embodiments of the method can include performing sealing cycles in the above recited seal times, consecutive sealing cycles, wet sealing, and other performance characteristics.

Another aspect of the present disclosure is directed to a sealed polymer tube, such as a polymer tube sealed by an IR tube sealer according to any of the embodiments described herein. For example, as described above, a seal produced by certain embodiments of an IR tube sealer described herein can have physically unique characteristics such as seal dimensions, seal quality, and seal integrity, which are able to be achieved in unparalleled quickness.

It is to be understood that the embodiments of the sealed polymer tube and its characteristics such as seal dimensions, seal quality and seal integrity described above equally apply to the embodiments directed to a sealed polymer tube. Accordingly, embodiments of the sealed polymer tube can include a sealed polymer tube having the above recited seal dimensions, midline indicator, seal quality such as lack of defects, maintenance of aseptic inner diameter, maintenance of air tight seal, and other properties as described above.

EXAMPLES

Example 1—Comparison of State of the Art Thermal Sealer to Embodiments of the Present Disclosure An IR tube sealer as depicted in FIG. 1 was compared with a Ceal-Flex sealer in their ability to seal Pharmed, a gamma irradiated sterilized TPV tubing material obtained from Saint-Gobain Performance Plastics Corporation in Clearwater, Fla. The Pharmed tubing tested has an inner diameter of ⅛ in and an outside diameter of ¼ in.

Figure 8:
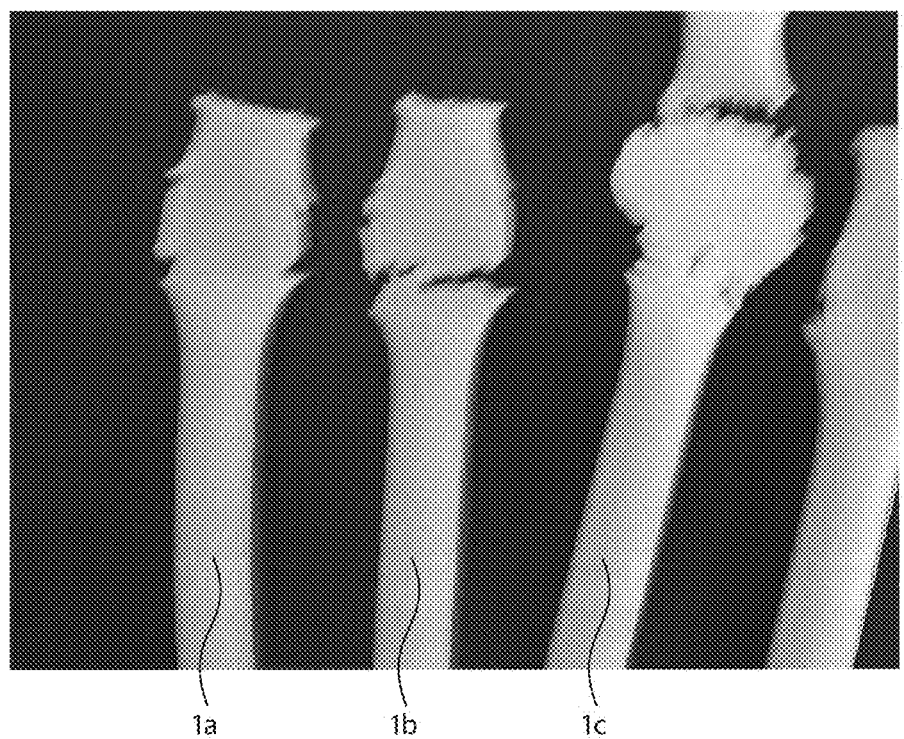
FIG. 8 includes a picture of tubes attempted to be sealed with a heat sealer.
Figure 9:
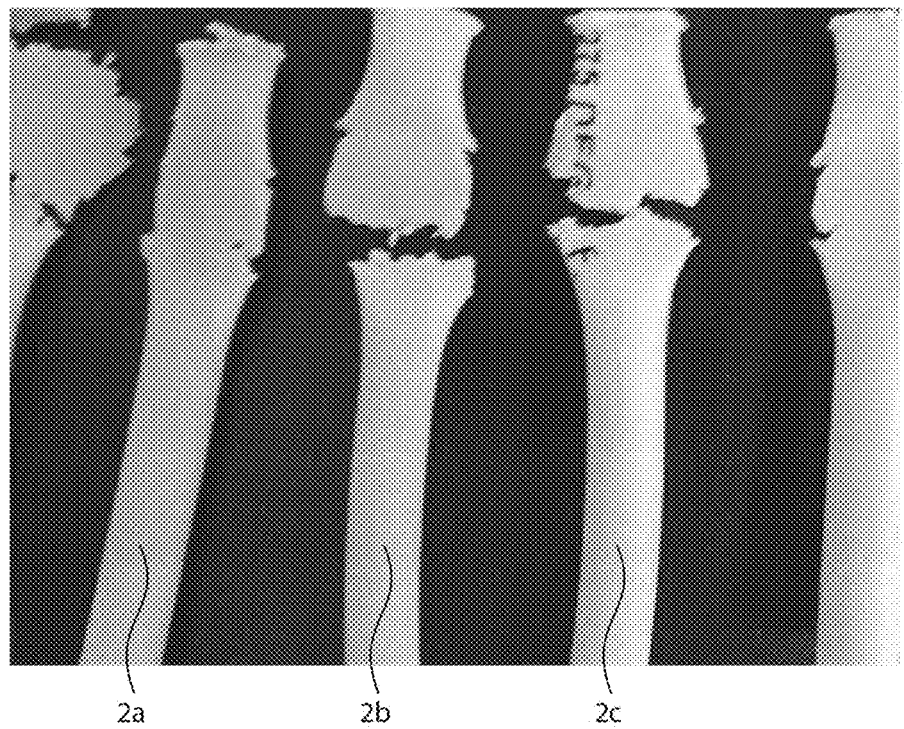
FIG. 9 includes a picture of tubes attempted to be sealed with a heat sealer.
Figure 10:
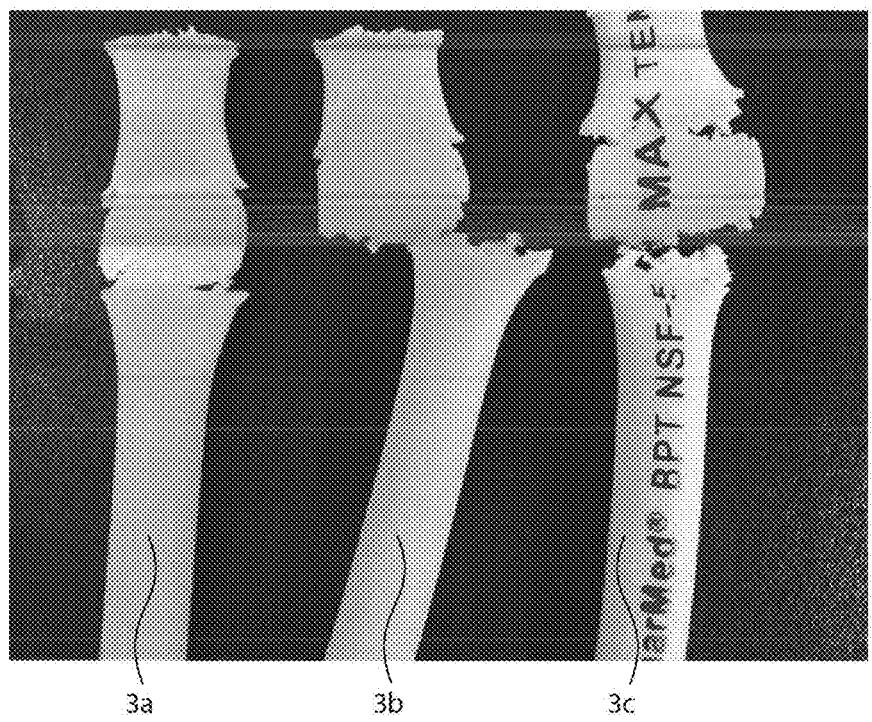
FIG. 10 includes a picture of tubes attempted to be sealed with a heat sealer.
Figure 11:
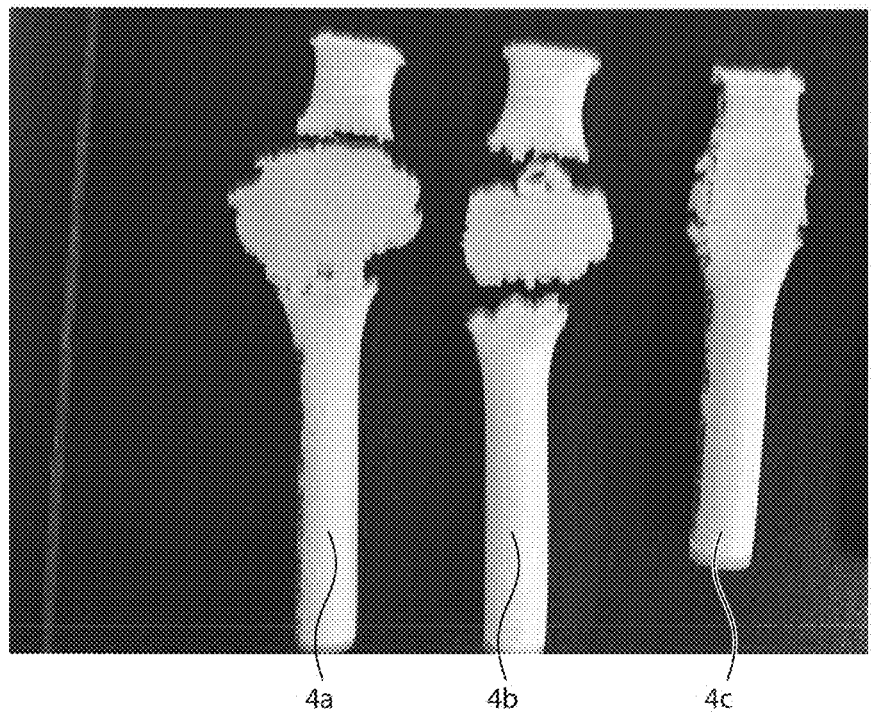
FIG. 11 includes a picture of tubes attempted to be sealed with a heat sealer.
Figure 12:
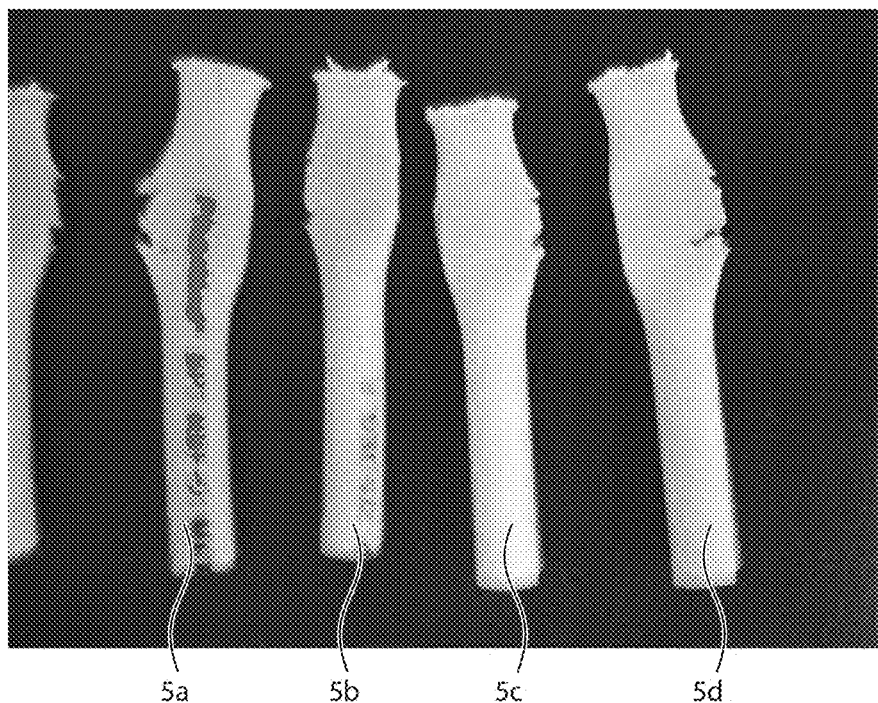
FIG. 12 includes a picture of tubes attempted to be sealed with a heat sealer.

Trials were conducted in which the Ceal-Flex Sealer had the settings of temperature, heating time and cooling time as indicated in Table 1 below. Images of the samples are represented in the figures. In particular, Trails 1a-1c are depicted in FIG. 8; trails 2a-2c are depicted in FIG. 9; trials 3a-3c are depicted in FIG. 10; trials 4a-4c are depicted in FIG. 11; and trials 5a-5d are depicted in FIG. 12.

TABLE 1

| Trial # | Temperature | Heating Time | Cooling Time | Air-tight Test |
|---------|-------------|--------------|--------------|----------------|
| 1a | 175 | 35 | 30 | fail* |
| 1b | 165 | 30 | 30 | fail* |
| 1c | 170 | 40 | 30 | fail* |
| 2a | 160 | 30 | 30 | fail* |
| 2b | 170 | 25 | 30 | fail* |
| 2c | 160 | 45 | 45 | fail* |
| 3a | 160 | 30 | 45 | fail* |
| 3b | 180 | 20 | 30 | fail* |
| 3c | 180 | 30 | 60 | fail* |
| 4a | 170 | 30 | 60 | fail* |
| 4b | 160 | 30 | 60 | fail* |
| 4c | 155 | 30 | 60 | fail* |
| 5a | 155 | 30 | 60 | fail* |
| 5b | 155 | 30 | 60 | fail* |
| 5c | 150 | 45 | 60 | fail* |
| 5d | 150 | 60 | 30 | fail* |

*Unable to test due to bad seal quality. See FIGS. 8 to 12.

Figure 13:
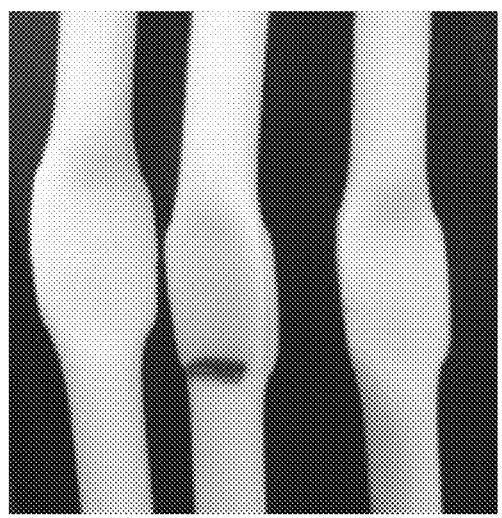
FIG. 13 includes a picture of tubes sealed with an IR sealer according to an embodiment of the present disclosure.

The IR tube sealing apparatus according to embodiments of the present disclosure was used to the seal the same Pharmed tubing tested with the Ceal-Flex sealer. The pictures of the sealed tubing material are depicted in FIG. 13. Each of the samples passed the air tight test at 15 psi for 30 minutes. The total seal time for each of the samples was in a range of 45 to 55 seconds, with a heating time of about 20 or about 30 seconds, and a cooling time of about 25 seconds.

As illustrated, the IR tube sealing apparatus according to the disclosure was able to quickly seal TPE tubing, and particularly a TPV tubing such as Pharmed. In contrast, state of the art thermal sealers such as Ceal-Flex was unable to form a high quality seal.

Example 2

A variety of sample tubes under the trade name C-Flex® and obtainable from Saint-Gobain Performance Plastics in Clearwater, Fla. was tested and compared for sealing versus a traditional thermal sealer and the IR sealer according to the present disclosure. The tubing was gamma irradiated at a dosage level of 40-50 kGy. The results of the heat sealing are provided in Table 2 and the results of the IR sealing are provided in Table 3.

TABLE 2

| | C-Flex Grade | Tube Size (ID × OD) (in) | Seal Length** (in) | Seal Width (in) | Seal Thickness (in) | Midline Feature | Air Test*** | Seal Time (min) |
|---|---|---|---|---|---|---|---|---|
| | Heat Sealed - Tubes were sealed with a Ceal-Flex thermal sealer | | | | | | | |
| 1 | -082 | 0.5 × 0.75 | 0.38 to 0.46 | 1.31 to 1.51 | 0.11 to 0.20 | No | Fail | 3 to 5 |
| 2 | -072 | 0.5 × 0.75 | 0.38 to 0.46 | 1.31 to 1.51 | 0.11 to 0.20 | No | Fail | 3 to 5 |

TABLE 2-continued

Heat Sealed - Tubes were sealed with a Ceal-Flex thermal sealer

| | C-Flex Grade | Tube Size (ID × OD) (in) | Seal Length** (in) | Seal Width (in) | Seal Thickness (in) | Midline Feature | Air Test*** | Seal Time (min) |
|---|---|---|---|---|---|---|---|---|
| 3 | Any grade | 1 × 1.5 | Could not be made through known thermal sealers | | | | | |
| 4 | -082, -072 | 0.125 × 0.25 | 0.41 to 0.46 | 0.64 to 1.01 | 0.034 to 0.67 | No | Pass | ~2 |

**Full seal.
***Half seal, integrity pressure testing at 15 psi for 30 min.

TABLE 3

IR Sealed - Tubes were sealed with an IR Sealer according to the Disclosure

| | C-Flex Grade | Tube Size (ID × OD) (in) | Seal Length** (in) | Seal Width (in) | Seal Thickness (in) | Midline Feature | Air Test*** | Seal Time |
|---|---|---|---|---|---|---|---|---|
| 1 | -082 | 0.5 × 0.75 | 0.87 to 0.97 | 1.10 to 1.28 | 0.12 to 0.20 | Yes | Pass | 99 s |
| 2 | -072 | 0.5 × 0.75 | 0.87 to 0.97 | 1.10 to 1.28 | 0.12 to 0.20 | Yes | Pass | 99 s |
| 3 | -082, -072 | 1 × 1.5 | 0.88 to 0.98 | 1.41 to 2.23 | 0.17 to 0.33 | Yes | Pass | 4 min |
| 4 | -082, -072 | 0.125 × 0.25 | 0.73 to 0.98 | 0.49 to 0.72 | 0.06 to 1.23 | Yes | Pass | 28 s |

**Full seal.
***Half seal, integrity pressure testing at 15 psi for 30 min.

As illustrated above, the IR sealer according to embodiments of the present disclosure was able to significantly reduce seal time, seal tubes that could not be sealed by heat sealers, and provide a higher quality, more robust seal. Further, the examples demonstrate that the IR sealer according to the disclosure can successfully perform wet sealing, while the traditional thermal sealers can not.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. An IR polymer tube sealing apparatus, the apparatus comprising:
  a. an IR lamp assembly; and
  b. a first contact plate and a second contact plate, wherein the first and second contact plates are adapted to reduce the distance between opposing side walls of a polymer tube; and
  c. wherein the apparatus is adapted to permanently weld together opposing sidewalls of a polymer tube and form an aseptic seal using the infrared radiation produced by the IR lamp assembly.

Item 2. An IR polymer tube sealing apparatus, the apparatus comprising:
  a. an IR lamp assembly; and
  b. a first contact plate and a second contact plate, wherein the first and second contact plates are adapted to reduce the distance between opposing side walls of a polymer tube; and
  c. wherein the apparatus is adapted to permanently weld together opposing sidewalls of a polymer tube and form a seal on the polymer using the infrared radiation produced by the IR lamp assembly; and
  i. wherein the seal forms an air tight seal as measured at 3 psi, 5 psi, 10 psi, 15 psi for 30 minutes;
  ii. and/or
  iii. a content of defects having a longest dimension of at least 0.5 mm of no greater than 3 defects per square centimeter.

Item 3. A portable, handheld IR polymer tube sealing apparatus, the apparatus comprising:
  a. a first IR lamp assembly and a first contact plate, wherein the first IR lamp assembly is adapted to produce infrared energy and is directed toward the contact plate;
  b. a second IR lamp assembly and a second contact plate, wherein the second IR lamp assembly is adapted to produce infrared energy and direct the infrared energy toward the second contact plate;
  c. wherein the first and second IR lamp assemblies are disposed generally opposite each other, and
  d. wherein the IR polymer tube sealing apparatus is adapted to receive and compress a polymer tube between the first and second contact plates; and
  e. wherein the IR polymer tube sealing apparatus is adapted to form a seal on the polymer tube through application of infrared energy toward the polymer tube.

Item 4. A portable handheld IR polymer tube sealing apparatus, wherein the apparatus is adapted to produce an aseptic and permanent seal on a polymer tube primarily through the application of infrared energy.

Item 5. An IR polymer tube sealing apparatus, the apparatus comprising:
  a. an IR lamp assembly adapted to produce infrared energy;

b. a first contact plate and a second contact plate, wherein the first and second contact plates are adapted to reduce the distance between opposing side walls of a polymer tube; and c. wherein the IR polymer tube sealing apparatus has a seal time of no greater than 120 seconds as measured according to the Sealing Time test under Sealing Time Test Condition 1, Sealing Time Test Condition 2, Sealing Time Test Condition 3, Sealing Time Test Condition 4, Sealing Time Test Condition 5, Sealing Time Test Condition 6, or a combination thereof.

Item 6. A portable, hand-held IR polymer tube sealing apparatus, the apparatus comprising:

a. an IR lamp assembly adapted to produce infrared energy;

b. a first contact plate and a second contact plate, wherein the first and second contact plates are adapted to reduce the distance between opposing side walls of a polymer tube; and c. wherein the apparatus is adapted to perform at least 30 consecutive sealing cycles while disconnected from an external power source, as measured according to the Consecutive Sealing Cycle Time test, under Consecutive Battery Sealing Test Condition 1, Consecutive Battery Sealing Test Condition 2, Consecutive Battery Sealing Test Condition 3, or a combination thereof, and wherein each of the at least 30 consecutive sealing cycles is performed in less than 120 seconds.

Item 7. An IR polymer tube sealing apparatus, the apparatus comprising:

a. an IR lamp assembly adapted to produce infrared energy;

b. a first contact plate and a second contact plate, wherein the first and second contact plates are adapted to reduce the distance between opposing side walls of a polymer tube; and c. wherein the apparatus is adapted to permanently seal together opposing sidewalls of the polymer tube using the infrared energy produced by the IR lamp assembly, and wherein the apparatus is adapted to release the force applied by the mechanism within 20 seconds after formation of the seal has been completed.

Item 8. A tube sealing apparatus, wherein the polymer tube sealing apparatus is adapted to form an airtight seal on a gamma irradiated or gamma sterilized TPV tubing material with a seal time of no greater than 120 seconds.

Item 9. A method for sealing a polymer tube, the method comprising:

a. providing an IR polymer tube sealing apparatus comprising:
  i. an IR lamp assembly adapted to produce infrared energy; and
  ii. a first contact plate and a second contact plate, wherein the first and second contact plates are adapted to reduce the distance between opposing side walls of a polymer tube; and b. inserting a polymer tube between the first and second contact plates;

c. reducing the distance between opposing side walls of the polymer tube; and d. irradiating the polymer tube such that a permanent aseptic seal is formed; and e. releasing the polymer tube such that the first and second contact plates are no longer providing a force to reduce the distance between opposing side walls of the polymer tube.

Item 10. A method for sealing a tube, the method comprising:

a. providing a tube sealing apparatus according to any one of the preceding claims; and b. sealing a tube.

Item 11. A polymer tube comprising a seal, wherein the seal is formed by the method of any one of the preceding claims.

Item 12. A polymer tube comprising a seal, wherein the seal is formed by the IR tube sealing apparatus of any one of the preceding claims.

Item 13. A polymer tube comprising an air-tight seal having a mid-line indicator generally disposed at the midline of the seal.

Item 14. The polymer tube, apparatus or method of any one of the preceding claims, wherein the apparatus is adapted to form a seal mid-line indicator generally disposed at the mid-line of the seal.

Item 15. The polymer tube, apparatus or method of any one of the preceding claims, wherein the mid-line indicator comprises a raised channel.

Item 16. The polymer tube, apparatus or method of any one of the preceding claims, wherein the mid-line indicator comprises a depressed groove.

Item 17. The polymer tube, apparatus or method of any one of the preceding claims, wherein the mid-line indicator has a different color than the color of the polymer tube.

Item 18. The polymer tube, apparatus or method of any one of the preceding claims, wherein the mid-line indicator is visually identifiable.

Item 19. The apparatus or method of any one of the preceding claims, wherein the apparatus comprises a first IR lamp assembly.

Item 20. The apparatus or method of any one of the preceding claims, wherein the apparatus comprises a first IR lamp assembly and a second IR lamp assembly.

Item 21. The apparatus or method of any one of the preceding claims, wherein the apparatus comprises a first IR lamp assembly and a second IR lamp assembly, and wherein the first IR lamp assembly is disposed generally opposite from the second IR lamp assembly such that infrared energy produced by each of the first and second IR lamp assemblies are directed toward each other.

Item 22. The apparatus or method of any one of the preceding claims, wherein the apparatus comprises a first IR lamp assembly and a second IR lamp assembly, and wherein the apparatus is adapted to receive and compress a polymer tube between the first IR lamp assembly and the second IR lamp assembly.

Item 23. The apparatus or method of any one of the preceding claims, wherein the apparatus comprises a first IR lamp assembly comprising an IR lamp and a second IR lamp assembly comprising an energy redirector, wherein the energy redirector is adapted to redirect energy from the IR lamp of the first IR lamp assembly.

Item 24. The apparatus or method of claim 23, wherein the second IR lamp assembly does not include a IR lamp.

Item 25. The apparatus or method of any one of the preceding claims, wherein the apparatus comprises a first contact plate and a second contact plate, and wherein the apparatus is adapted to receive and compress a polymer tube between the first contact plate and the second contact plate.

Item 26. The apparatus or method of any one of the preceding claims, wherein the first and/or second contact plates are movable to compress a polymer tube.

Item 27. The apparatus or method of any one of the preceding claims, wherein at least part of the first and/or second IR lamp assemblies are movable to compress a polymer tube.

Item 28. The apparatus or method of any one of the preceding claims, wherein the apparatus is portable.

Item 29. The apparatus or method of any one of the preceding claims, wherein the apparatus is hand-held.

Item 30. The apparatus or method of any one of the preceding claims, wherein the apparatus further comprises a battery.

Item 31. The apparatus or method of any one of the preceding claims, wherein the apparatus further comprises a handle.

Item 32. The apparatus or method of any one of the preceding claims, wherein the handle is adapted to receive at least one had of a user, and support the user in transporting the apparatus.

Item 33. The apparatus or method of any one of the preceding claims, wherein the handle is adapted to receive at least one had of a user, and support the user in transporting the apparatus, and wherein the apparatus comprises a button that is engagable with the same hand of the user that is grasping the handle.

Item 34. The apparatus or method of any one of the preceding claims, wherein the apparatus has a weight of less than about 10 lbs.

Item 35. The apparatus or method of any one of the preceding claims, wherein the apparatus is adapted to perform at least 40 consecutive sealing cycles while not being physically connected to an external power source as measured when consecutively sealing thermoplastic tubes having an outside diameter in a range of about 0.250 inches to 0.375 inches.

Item 36. The apparatus or method of any one of the preceding claims, wherein the apparatus is adapted to perform at least 30 consecutive sealing cycles while not being physically connected to an external power source as measured when consecutively sealing thermoplastic tubes having an outside diameter in a range of about 0.375 inches to 0.750 inches.

Item 37. The apparatus or method of any one of the preceding claims, wherein the apparatus is adapted to perform at least 25, at least 30, at least 35, at least 40, at least 45, at least 50, at least 55, at least 60, at least 65, at least 70, or even at least 75 consecutive sealing cycles while not being physically connected to an external power source as measured when consecutively sealing thermoplastic tubes having an outside diameter of about 0.375 inches.

Item 38. The apparatus or method of any one of the preceding claims, wherein the apparatus is adapted to perform at least 25, at least 30, at least 35, at least 40, at least 45, at least 50, at least 55, at least 60, at least 65, at least 70, or even at least 75 consecutive sealing cycles while not being physically connected to an external power source as measured when consecutively sealing tubes having an outside diameter of about 0.75 inches.

Item 39. The apparatus or method of any one of the preceding claims, wherein the apparatus is adapted to have a seal time of no more than 150 seconds, no more than 140 seconds, no more than 130 seconds, no more than 120 seconds, no more than 110 seconds, no more than 100 seconds, no more than 90 seconds, no more than 80 seconds, no more than 70 seconds, 60 seconds, no more than 55 seconds, no more than 50 seconds, no more than 45 seconds, no more than 40 seconds, no more than 35 seconds, no more than 30 seconds, or even no more than 25 seconds as measured according to the Sealing Time test on a thermoplastic tube having an outside diameter in a range of about 0.25 inches to 1.5 inches.

Item 40. The apparatus or method of any one of the preceding claims, wherein the apparatus is adapted have a seal time of no more than 150 seconds, no more than 140 seconds, no more than 130 seconds, no more than 120 seconds, no more than 110 seconds, no more than 100 seconds, no more than 90 seconds, no more than 80 seconds, no more than 70 seconds, 60 seconds, no more than 55 seconds, no more than 50 seconds, no more than 45 seconds, no more than 40 seconds, no more than 35 seconds, no more than 30 seconds, or even no more than 25 seconds as measured according to the Sealing Time test on a thermoplastic tube having an outside diameter of about 0.375 inches.

Item 41. The apparatus or method of any one of the preceding claims, wherein the apparatus is adapted have a seal time of no more than no more than 150 seconds, no more than 140 seconds, no more than 130 seconds, no more than 120 seconds, no more than 110 seconds, no more than 100 seconds, no more than 90 seconds, no more than 80 seconds, no more than 70 seconds, 60 seconds, no more than 55 seconds, no more than 50 seconds, no more than 45 seconds, no more than 40 seconds, no more than 35 seconds, no more than 30 seconds, or even no more than 25 seconds as measured according to the Sealing Time test on a thermoplastic tube having an outside diameter of about 0.5 inches.

Item 42. The apparatus or method of any one of the preceding claims, wherein the apparatus is adapted to have a seal time of no more than no more than 150 seconds, no more than 140 seconds, no more than 130 seconds, no more than 120 seconds, no more than 110 seconds, no more than 100 seconds, no more than 90 seconds, no more than 80 seconds, no more than 70 seconds, 60 seconds, no more than 55 seconds, no more than 50 seconds, no more than 45 seconds, no more than 40 seconds, no more than 35 seconds, no more than 30 seconds, or even no more than 25 seconds as measured according to the Sealing Time test on a thermoplastic tube having an outside diameter of about 0.75 inches.

Item 43. The apparatus or method of any one of the preceding claims, wherein the polymer tube comprises a thermoplastic, a thermoplastic elastomer (TPE), a braided TPE, a thermoplastic vulcanizate (TPV), or combinations thereof.

Item 44. The apparatus or method of any one of the preceding claims, wherein the apparatus is adapted to seal a biopharmaceutical tube.

Item 45. The apparatus or method of any one of the preceding claims, wherein the apparatus is adapted to seal a gamma irradiated or gamma sterilized tube.

Item 46. The apparatus or method of any one of the preceding claims, wherein the polymer tube has a hardness of at least 30 durometer, at least 35 durometer, or even at least 40 durometer as measured according to ASTM D2240.

Item 47. The apparatus or method of any one of the preceding claims, wherein the polymer tube has a hardness of no greater than 100 durometer, no greater than 90 durometer, or even no greater than 80 durometer as measured according to ASTM D2240.

Item 48. The apparatus or method of any one of the preceding claims, wherein the polymer tube has a hardness of in a range of 30 durometer to 100 durometer, 35 durometer to 90 durometer, or even 40 durometer to 80 durometer as measured according to ASTM D2240.

Item 49. The apparatus or method of any one of the preceding claims, wherein an inner cavity of the polymer tube is aseptic during sealing.

Item 50. The apparatus or method of any one of the preceding claims, wherein the apparatus is adapted to maintain the sterility of an inner cavity of the polymer tube after sealing.

Item 51. The apparatus or method of any one of the preceding claims, wherein the seal has a content of defects having a longest dimension of at least 0.5 mm of no greater than 10 defects per square centimeter, no greater than 5 defects per square centimeter, no greater than 3 defects per square centimeter, no greater than 2 defects per square centimeter, or even no greater than 1 air bubble per square centimeter.

Item 52. The apparatus or method of any one of the preceding claims, wherein the seal is essentially free of defects having a longest dimension of at least 0.5 mm.

Item 53. The apparatus or method of any one of the preceding claims, wherein the apparatus is adapted to form a seal having a ratio of a seal length $S_L$ to an outside diameter of the unsealed tube $T_{OD}$ of at least about 0.5, at least about 0.9, at least about 1.1, at least about 1.5, or even at least about 2.0.

Item 54. The apparatus or method of any one of the preceding claims, wherein the apparatus is adapted to form a seal having a ratio of a seal length $S_L$ to an outside diameter of the unsealed tube $T_{OD}$ of no greater than 10, no greater than 8, or even no greater than 5.

Item 55. The apparatus or method of any one of the preceding claims, wherein the apparatus is adapted to form a seal having a ratio of seal outside diameter $S_{OD}$ to the outside diameter of the unsealed tube $T_{OD}$ of at least about 1.01, at least about 1.1, at least about 1.2, or even at least about 1.3.

Item 56. The apparatus or method of any one of the preceding claims, wherein the apparatus is adapted to form a seal having a ratio of seal outside diameter $S_{OD}$ to the outside diameter of the unsealed tube $T_{OD}$ of no greater than 5, no greater than 3, or even no greater than 2.

Item 57. The apparatus or method of any one of the preceding claims, wherein the apparatus is adapted to forma seal having a length of at least about 0.51 inches, at least about 0.6 inches, or even at least about 0.8 inches.

Item 58. The apparatus or method or method of any one of the preceding claims, wherein the apparatus is adapted to form an essentially airtight seal as tested with an air pressure of 15 psi for 30 minutes.

Item 59. The apparatus of any one of the preceding claims, wherein the apparatus is adapted to wet seal a polymer tube.

Item 60. The polymer tube of any one of the preceding claims, wherein the seal is a wet seal.

Item 61. The method of any one of the preceding claims, wherein the method comprises wet sealing the polymer tube.

Item 62. The apparatus of any one of the preceding claims, wherein the apparatus is adapted to initiate application of infrared energy before fully compressing the tube.

Item 63. The method of any one of the preceding claims, wherein the method comprises initiating application of infrared energy before fully compressing the tube.

Item 64. The apparatus of any one of the preceding claims, wherein the apparatus is adapted to initiate pressurized cooling immediately after application of infrared energy.

Item 65. The apparatus of any one of the preceding claims, wherein the apparatus is adapted to initiate pressurized cooling during application of infrared energy.

Item 66. The method of any one of the preceding claims, wherein the method comprises initiating pressurized cooling immediately after application of infrared energy.

Item 67. The method of any one of the preceding claims, wherein the method comprises initiating pressurized cooling during application of infrared energy.

Item 68. The sealed tube, method or apparatus of any one of the preceding claims, wherein the sealed tube complies with a sub visible particle content as measured according to United States Pharmacopoeia standard <788>.

Item 69. The sealed tube, method or apparatus of any one of the preceding claims, wherein the sealed tube complies with a pH standard according to United States Pharmacopoeia standard <661>.

Item 70. The sealed tube, method or apparatus of any one of the preceding claims, wherein the sealed tube complies with a conductivity standard according to United States Pharmacopoeia standard <645>.

Item 71. The sealed tube, method or apparatus of any one of the preceding claims, wherein the sealed tube complies with a NVR standard according to United States Pharmacopoeia standard <661>.

Item 72. The sealed tube, method or apparatus of any one of the preceding claims, wherein the sealed tube complies with a Endotoxin standard according to United States Pharmacopoeia standard <85>.

Item 73. The sealed tube, method or apparatus of any one of the preceding claims, wherein the sealed tube complies with a Cyotoxicity standard according to United States Pharmacopoeia standard MEM elution.

Item 74. The sealed tube, method or apparatus of any one of the preceding claims, wherein the sealed tube complies with a total organic carbon (TOC) standard according to United States Pharmacopoeia standard <643>.

Item 75. The sealed tube, method or apparatus of any one of the preceding claims, wherein the sealed tube has an air pressure test rating of at least about 3 psi, at least about 5 psi, at least about 8 psi, at least about 10 psi, at least about 12 psi, or even at least about 15 psi at 30 minutes as measured under Aged Pressure Test Condition 1, Aged Pressured Test Condition 2, Aged Pressure Test Condition 3 after natural aging at ambient conditions for 6 months, 1 year, 18 months, 2 years, or even 3 years.

Item 76. The sealed tube, method or apparatus of any one of the preceding claims, wherein the sealed tube has an air pressure test rating of at least about 3 psi, at least about 5 psi, at least about 8 psi, at least about 10 psi, at least about 12 psi, or even at least about 15 psi at 30 minutes as measured under Aged Pressure Test Condition 1, Aged Pressured Test Condition 2, Aged Pressure Test Condition 3 after simulated aging at 55 degrees Celsius for 20 days, 40 days, 60 days, 80 days, or even 120 days according to ASTM F1980.

Item 77. The sealed tube, method or apparatus of any one of the preceding claims, wherein the sealed tube maintains compliance with the standards of sub visible particulates, pH, conductivity, NVR, endotoxin, cytotoxicity, genotoxicity, TOC, or combinations thereof after natural aging at ambient conditions for 6 months, 1 year, 18 months, 2 years, or even 3 years.

Item 78. The sealed tube, method or apparatus of any one of the preceding claims, wherein the sealed tube maintains compliance with the standards of sub visible particulates, pH, conductivity, NVR, endotoxin, cytotoxicity, genotoxicity, TOC, or combinations thereof after simulated aging at 55 degrees Celsius for 20 days, 40 days, 60 days, 80 days, or even 120 days according to ASTM F1980.

Item 79. The sealed tube, method or apparatus of any one of the preceding claims, wherein the sealed tube maintains seal integrity after natural aging at ambient conditions for 6 months, 1 year, 18 months, 2 years, or even 3 years.

Item 80. The sealed tube, method or apparatus of any one of the preceding claims, wherein the sealed tube maintains seal integrity after simulated aging at 55 degrees Celsius for 20 days, 40 days, 60 days, 80 days, or even 120 days according to ASTM F1980.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. An IR polymer tube sealing apparatus, the apparatus comprising:
   a. an IR lamp assembly; and
   b. a first contact plate and a second contact plate, wherein the first and second contact plates are adapted to reduce the distance between opposing side walls of a polymer tube; and
   c. a handle and a button positioned on the handle such that a user can hold the claimed apparatus and press the button at the same time with a single hand,
   wherein the apparatus is adapted to permanently weld together opposing sidewalls of a polymer tube and form an aseptic seal using the infrared radiation produced by the IR lamp assembly, wherein the first and second contact plates are configured to contact the polymer tube, and wherein at least one of the first contact plate or the second contact plate contains a seal region which allows infrared energy produced by the IR lamp assembly to substantially passes through at least one of the first contact plate or the second contact plate, wherein the IR polymer tube sealing apparatus is portable, wherein the IR lamp assembly comprises a first IR lamp assembly and a second IR lamp assembly, wherein the entire apparatus is hand-held, wherein the IR polymer tube sealing apparatus has a weight of less than about 10 lbs.

2. The apparatus of claim 1, wherein the seal forms an air tight seal as measured at 3 psi, 5 psi, 10 psi, and 15 psi for 30 minutes.

3. The apparatus of claim 1, wherein a content of defects having a longest dimension of at least 0.5 mm of no greater than 3 defects per square centimeter.

4. The apparatus of claim 1, wherein the IR polymer tube sealing apparatus has a seal time of no greater than 120 seconds as measured according to the Sealing Time test under Sealing Time Test Condition 1, Sealing Time Test Condition 2, Sealing Time Test Condition 3, Sealing Time Test Condition 4, Sealing Time Test Condition 5, Sealing Time Test Condition 6, or a combination thereof.

5. The apparatus of claim 1, wherein the apparatus is a portable, handheld IR polymer tube sealing apparatus.

6. The apparatus of claim 1, wherein the apparatus is adapted to perform at least 30 consecutive sealing cycles while disconnected from an external power source, as measured according to the Consecutive Sealing Cycle Time test, under Consecutive Battery Sealing Test Condition 1, Consecutive Battery Sealing Test Condition 2, Consecutive Battery Sealing Test Condition 3, or a combination thereof, and wherein each of the at least 30 consecutive sealing cycles is performed in less than 120 seconds.

7. The apparatus of claim 1, wherein the apparatus is adapted to permanently seal together opposing sidewalls of the polymer tube using the infrared energy produced by the IR lamp assembly, and wherein the apparatus is adapted to release the force applied by the mechanism within 20 seconds after formation of the seal has been completed.

8. The apparatus of claim 1, wherein the first IR lamp assembly is disposed generally opposite from the second IR lamp assembly such that infrared energy produced by each of the first and second IR lamp assemblies are directed toward each other.

9. The apparatus of claim 1, wherein the apparatus comprises a first IR lamp assembly and a second IR lamp assembly, and wherein the apparatus is adapted to receive and compress a polymer tube between the first IR lamp assembly and the second IR lamp assembly.

10. The apparatus of claim 1, wherein the apparatus comprises a first IR lamp assembly comprising an IR lamp and a second IR lamp assembly comprising an energy redirector, wherein the energy redirector is adapted to redirect energy from the IR lamp of the first IR lamp assembly.

11. The apparatus of claim 1, wherein an inner cavity of the polymer tube is aseptic during sealing.

12. The apparatus of claim 1, wherein the apparatus is adapted to maintain the sterility of an inner cavity of the polymer tube after sealing.

13. The apparatus of claim 1, wherein the seal is essentially free of defects having a longest dimension of at least 0.5 mm.

14. The apparatus of claim 1, wherein the polymer tube comprises a thermoplastic, a thermoplastic elastomer (TPE), a braided TPE, a thermoplastic vulcanizate (TPV), or combinations thereof.

15. The apparatus of claim 1, wherein the apparatus is adapted to seal a biopharmaceutical tube.

16. The apparatus of claim 1, wherein the first contact plate and the second contact plate contact the polymer tube and contain a seal region which allows the infrared energy to pass through at least one of the first contact plate or the second contact plate and interact with the polymer tube.

17. The apparatus of claim 1, further comprising a handle.

18. A IR polymer tube sealing apparatus, the apparatus comprising:
   a. a first IR lamp assembly and a first contact plate, wherein the first IR lamp assembly is adapted to produce infrared energy and is directed toward the contact plate;
   b. a second IR lamp assembly and a second contact plate, wherein the second IR lamp assembly is adapted to produce infrared energy and direct the infrared energy toward the second contact plate; and
   c. a handle and a button positioned on the handle such that a user can hold the claimed apparatus and press the button at the same time with a single hand, wherein the first and second IR lamp assemblies are disposed generally opposite each other; wherein the IR polymer tube sealing apparatus is adapted to receive and compress a polymer tube between the first and second contact plates; and
   wherein the IR polymer tube sealing apparatus is adapted to form a seal on the polymer tube through application of infrared energy toward the polymer tube, wherein the IR polymer tube sealing apparatus is portable, wherein the entire apparatus is hand-held, wherein the IR polymer tube sealing apparatus has a weight of less than about 10 lbs.

* * * * *